United States Patent [19]

Wooden et al.

[11] Patent Number: 5,492,564
[45] Date of Patent: Feb. 20, 1996

[54] DIKETOPYRROLOPYRROLE PIGMENT WITH HIGH CHROMA

[75] Inventors: Gary Wooden, Oberschrot; Ingo Schlöder, Matran; Olof Wallquist, Marly, all of Switzerland

[73] Assignee: Ciba-Geigy Corporation, Tarrytown, N.Y.

[21] Appl. No.: 216,703

[22] Filed: Mar. 23, 1994

[30] Foreign Application Priority Data

Mar. 16, 1994 [CH] Switzerland .................... 780/94

[51] Int. Cl.⁶ .................................... C07D 471/02
[52] U.S. Cl. .................... 106/493; 106/494; 106/498; 106/499
[58] Field of Search .................... 106/493, 494, 106/498, 499

[56] References Cited

U.S. PATENT DOCUMENTS

| | | | |
|---|---|---|---|
| 4,579,949 | 4/1986 | Rochat et al. | 546/167 |
| 4,632,704 | 12/1986 | Bäbler | 106/498 |
| 4,720,305 | 1/1988 | Igbal et al. | 106/494 |
| 4,778,899 | 10/1988 | Pfenninger et al. | 548/453 |
| 4,931,566 | 6/1990 | Surber et al. | 548/453 |
| 4,992,101 | 2/1991 | Jaffe | 106/498 |

FOREIGN PATENT DOCUMENTS

| | | |
|---|---|---|
| 0181290 | 5/1986 | European Pat. Off. |
| 0184982 | 6/1986 | European Pat. Off. |
| 0190999 | 8/1986 | European Pat. Off. |
| 0302018 | 2/1989 | European Pat. Off. |
| 0337435 | 10/1989 | European Pat. Off. |

OTHER PUBLICATIONS

CRC Handbook of Chemistry and Physics, 64th ed., R. C. West, Ed., p. D–12, No. 47, 1984, CRC Press, Boca Raton, FL.

*Primary Examiner*—Mark L. Bell
*Assistant Examiner*—Scott L. Hertzog
*Attorney, Agent, or Firm*—Michele A. Kovaleski

[57] ABSTRACT

The pigment form of the diketopyrrolopyrrole pigment of formula

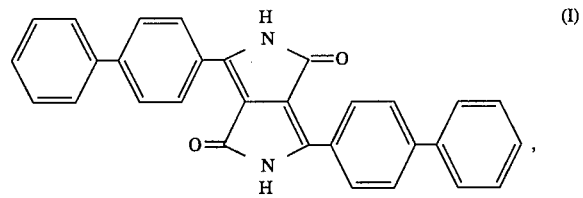

having high saturation, characterised by a chroma $C^*_{ab}$ of at least 45 in the CIELAB system when incorporated in a plasticised PVC pressed sheet. This pigment has superior opacity and an unexpectedly high chroma.

11 Claims, No Drawings

DIKETOPYRROLOPYRROLE PIGMENT WITH HIGH CHROMA

The present invention relates to a novel pigment form of 1,4-diketo-3,6-bis(biphenyl-4-yl)-pyrrolo[ 3,4-c]pyrrole having unexpectedly high chroma.

1,4-Diketo-3,6-bis(biphenyl-4-yl)-pyrrolo[3,4-c]pyrrole is disclosed in U.S. Pat. No. 4,579,949. This pigment is more a transparent form having a chroma insufficient for specific utilities. U.S. Pat. No. 4,931,566 discloses a novel method of preparing chemically purer pyrrolo[3,4-c]pyrroles also with enhanced coloristic properties, including improved saturation, i.e. chroma, which method comprises carrying out the protolysis of the pigment alkali metal salt sequentially, i.e. in at least two portions. The 1,4-diketo-3,6-bis(biphenyl-4-yl)-pyrrolo[3,4-c]pyrrole disclosed in this patent is distinguished by markedly enhanced opacity and a somewhat better, but still unsatisfactory, chroma. For specific utilities, typically in plastics and, in particular, in non-metallised automotive and industrial lacquers, as high a saturation as possible is of the first importance. Recently, the demand for high-performance pigments with particularly high saturation has therefore risen appreciably. A number of diketopyrrolopyrrole pigments have found acceptance as high-performance pigments, but the problem has been to obtain a form, even of such highly regarded pigments, which has a particularly high saturation.

Surprisingly, it has now been found that in the synthesis of 1,4-diketo-3,6-bis(biphenyl-4-yl)pyrrolo[ 3,4-c]pyrrole a product having high opacity and unexpectedly very high saturation is obtained by carrying out the protolysis of the pigment salt formed as intermediate and the subsequent conditioning by adding the suspension of the pigment salt to a lower alkyl alcohol in the temperature range from 65° to 150° C. in one portion.

Accordingly, the invention relates to a pigment form of the diketopyrrolopyrrole pigment of formula

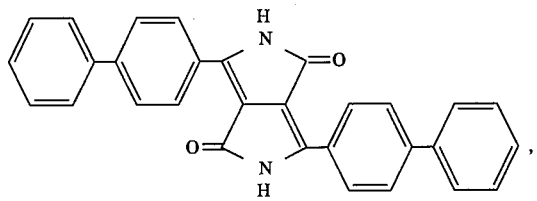
(I)

having high saturation, characterised by a chroma $C^*_{ab}$ of at least 45 in the CIELAB system in a full-shade plasticised PVC pressed sheet prepared in accordance with DIN 53 775, part 2, and having a pigment concentration of 1% and a thickness of 1.0 mm.

Preferred diketopyrrolopyrroles of formula I are distinguished by

—a chroma $C^*_{ab}$ of at least 46, preferably from 46.3 to 54,

—a lightness $L^*$ of at least 36, preferably from 36.5 to 42 and

—a hue angle $h_{ab}$ of at least 23, preferably from 23.4 to 29 in the CIELAB system, in a plasticised PVC sheet prepared as described above.

The terms "chroma" or "chromaticity" ($C^*_{ab}$), lightness ($L^*$) and hue angle ($h_{ab}$) used in the CIELAB system are known from the literature, inter alia from H. G. Völz, Industrielle Farbprüfung, Grundlagen und Methoden, VCH Verlagsgesellschaft mbH, Weinheim, D, 1990. It is merely emphasised here that the terms chroma or chromaticity are equivalent to saturation.

It will be readily understood that the diketopyrrolopyrrole of this invention is distinguished by the unexpectedly high saturation not only in PVC, but in all substrates for the pigmentation of which it may suitably be used. PVC has been chosen in the present context solely as reference substrate for the quantitative determination of saturation, because suitable test specimens (pressed sheets) can be prepared by a simple standard (DIN 53 775, Pan 2). As already indicated, the pigment of this invention also has surprisingly high saturation in other plastics as well as in paint systems.

The process for the preparation of the pigment of this invention, which process is novel and is also an object of the invention, by reacting 1 mol of a dicyclohexyl succinate, dialkyl succinate, monoalkylmonophenyl or diphenyl succinate, in which succinates alkyl is $C_1$–$C_{18}$alkyl and phenyl is unsubstituted phenyl or phenyl which is substituted by one or two halogen atoms, one or two $C_1$–$C_6$alkyl or $C_1$–$C_6$alkoxy groups, with 2 mol of a nitrile of formula

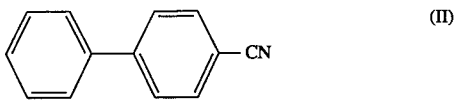
(II)

in an inert organic solvent and in the presence of an alkali metal or of an alkali metal alcoholate as strong base, at elevated temperature, to give a pigment alkali metal salt, and subsequently generating a compound of formula I by protolysis of the resultant pigment alkali metal salt and subsequent conditioning, comprising adding a suspension of said pigment alkali metal salt to water and an alcohol ROH, wherein R is $C_2$–$C_4$alkyl, in the temperature range from 65° to 150° C., and treating the pigment suspension for 30 minutes to 24 hours also in the temperature range from 65° to 150° C.

$C_1$–$C_6$Alkyl is typically methyl, ethyl, n-propyl, isopropyl, n-butyl, sec-butyl, tert-butyl, n-amyl, tert-amyl, hexyl, and $C_1$–$C_{18}$alkyl may additionally be heptyl, octyl, 2-ethylhexyl, nonyl, decyl, dodecyl, tetradecyl, hexadecyl or octadecyl.

$C_1$–$C_6$Alkoxy is typically methoxy, ethoxy, n-propoxy, isopropoxy, butoxy or hexyloxy.

The alcohol ROH is conveniently isopropanol or n-butanol, but is more particularly propanol and, most preferably, ethanol.

The suspension of the pigment alkali metal salt is preferably added to a mixture of water/alcohol, the mixture ratio of water to alcohol conveniently being 5–50:95–50, preferably 10–30:90–70% by volume The protolysis and the subsequent conditioning are carried out in basic to neutral medium. A basic medium is preferred and the preferred temperature range is from 70° to 115° C., for 1 to 8 hours.

The dialkyl or diphenyl succinates to be used in the practice of this invention may be symmetrical or asymmetrical disuccinates. It is, however, preferred to use symmetrical disuccinates, in particular symmetrical dialkyl succinates. If a diphenyl or monophenyl-monoalkyl succinate is used, then phenyl may typically be unsubstituted or phenyl or phenyl which is substituted by one or two halogen atoms, typically chlorine atoms, one or two $C_1$–$C_6$alkyl groups such as methyl, ethyl, isopropyl or tert-butyl, or one or two $C_1$–$C_6$-alkoxy groups such as methoxy or ethoxy. Phenyl is preferably unsubstituted phenyl. If a dialkyl succinate or a monoalkylmonophenyl succinate is used, then alkyl may be unbranched or branched, and may preferably contain 1 to 12, most preferably 1 to 8 and, most preferably, 1 to 5 carbon atoms. Branched alkyl is preferably sec- or tert-alkyl, typically isopropyl, sec-butyl, ten-butyl and tert-amyl. It is most preferred to use symmetrical branched dialkyl succinates in which each alkyl moiety contains 3 to 5 carbon atoms.

Illustrative examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, bis[ 1,1-dimethylbutyl] succinate, bis[ 1,1,3,3-tetramethylbutyl] succinate, bis[ 1,1-dimethylpentyl] succinate, his[ 1-methyl- 1-ethylbutyl] succinate, bis[ 1,1-diethylpropyl] succinate, diphenyl succinate, bis[4-methylphenyl] succinate, bis[2-methylphenyl] succinate, bis[4-chlorophenyl] succinate, bis[2,4-dichlorphenyl] succinate, and monoethyl-monophenyl succinate.

The above mentioned disuccinates and the nitrile of formula II are known compounds and can be prepared by known processes.

The reaction of the disuccinate with the nitrile of formula II is carried out in an organic solvent. Suitable solvents are typically primary, secondary or tertiary alcohols containing 1 to 10 carbon atoms, including methanol, ethanol, n-propanol, isopropanol, n-butanol, sec-butanol, ten-butanol, n-pentanol, 2-methyl-2-butanol, 2-methyl-2-pentanol, 3-methyl-3-pentanol, 2-methyl-2-hexanol, 3-ethyl-3-pentanol and 2,4,4-trimethyl-2-pentanol; glycols, such as ethylene glycol or diethylene glycol; and also ethers such as tetrahydrofuran or dioxane, or glycol ethers such as ethylene glycol mono- or dimethyl ether, ethylene glycol mono- or diethyl ether, diethylene glycol monomethyl ether or diethylene glycol monoethyl ether; as well as dipolar aprotic solvents, including dimethyl formamide, N,N-dimethylacetamide, nitrobenzene and N-methylpyrrolidone; aliphatic or aromatic hydrocarbons such as benzene or alkyl alkoxy- or halogen-substituted benzene, toluene, xylenes, anisole or chlorobenzene; or aromatic N-heterocycles such as pyridine, picoline or quinoline. Mixtures of the above solvents can also be used. It is preferred to use 5–20 parts by weight of solvent per 1 part by weight of reactant.

The preferred solvent in the process of this invention is an alcohol, especially a secondary or tertiary alcohol. Preferred tertiary alcohols are tert-butanol and tert-amyl alcohol. Also preferred are mixtures thereof, or mixtures of preferred solvents with aromatic hydrocarbons such as toluene or xylenes, or with halogen-substituted benzenes such as chlorobenzene or o-dichlorobenzene.

Strong bases suitable for use in the practice of this invention are alkali metals such as lithium, sodium and potassium, and alkali metal alcoholates which are derived preferably from primary, secondary or tertiary aliphatic alcohols containing 1 to 10 carbon atoms, including typically the methylates, ethylates, n-propylates, isopropylates, n-butylates, sec-butylates, tert-butylates, 2-methyl-2-butylates, 2-methyl-2-pentylates, 3-methyl-3-pentylates and 3-ethyl-3-pentylates of lithium, sodium or potassium. It is, however, also possible to use a mixture of the aforementioned alkali metal alcoholates. It is preferred to use alkali metal alcoholates in which the alkali is preferably sodium or potassium, and the alcoholate is preferably derived from a secondary or tertiary alcohol. Particularly preferred strong bases are therefore typically sodium or potassium isopropylate, sec-butylate, tert-butylate and tert-amylate. The alkali metal alcoholates can also be prepared in situ by reacting the corresponding alcohol with the alkali metal.

In the process of this invention, the strong base may conveniently be used in an mount of 0.1 to 10 tool, preferably from 1.9 to 4.0 mol, based on 1 mol of the disuccinate.

Although in principle stoichiometric amounts of base will suffice, an excess of base will often have a beneficial influence on the yield.

The reaction may conveniently be carded out in the temperature range from 60° to 140° C., but preferably from 80° to 120° C.

To react the disuccinate with the nitrile of formula II it is in principle possible to bring all the components together at low temperature and then to heat the mixture to the range of the reaction temperature, or to add the individual components in any order in the range of the reaction temperature. A preferred embodiment that usually has a particularly beneficial influence on the yield comprises bringing the nitrile together with the strong base, heating the mixture, and adding the disuccinate in the range of the reaction temperature. A further possibility comprises simultaneously adding the disuccinate and the nitrile to the base. It is entirely possible to carry out the inventive process not only batchwise, but also continuously.

Especially when using disuccinates containing alkyl radicals and alcoholates derived from lower alcohols such as methanol, ethanol, n-propanol, isopropanol or ten-butanol, it may be advantageous to remove the lower alcohol that forms during the reaction from the reaction medium continuously in order to obtain higher yields.

If an alcohol is used as solvent and an alcoholate as base, then it may be advantageous to choose an alcohol and an alcoholate containing the same alkyl groups. In addition, it may likewise be advantageous if the disuccinate also contains such alkyl groups.

For the protolysis of the resultant pigment salt, the pigment alkali salt is added to the protolysing agent consisting of water and alcohol. After treating the resultant suspension in the temperature range from 65° to 150° C. for 30 minutes to 24 hours, the pigment of formula I precipitates and can be isolated by per se known separating methods such as filtration. The water/alcohol mixture can be used in any mixture ratios from 5 to 20 parts by weight per 1 part of the pigment alkali salt.

The pigment of this invention has excellent suitability for pigmenting organic material of high molecular weight. It may be typically used as a powder, paste, flush paste and formulation and is suitable, inter alia, for incorporation in printing inks, size colors, binder colors or paint systems of all kinds, including physically drying and oxidatively drying paints, acid-, amine- and peroxide-curing paints or polyurethane paints. The pigment can also be used for coloring synthetic, semi-synthetic or natural macromolecular materials, including polyvinyl chloride, polystyrene, polyolefins, for example polyethylene and polypropylene and also polyesters, phenolic plastics, aminoplasts and rubber. Further utilities are for coloring natural, regenerated or man-made fibres such as glass, silicate, asbestos, wood, cellulose, acetyl cellulose, polyacrylonitrile, polyester, polyurethane and polyvinyl chloride fibres or mixtures thereof, without or together with other organic or inorganic pigments. With the novel pigment there are obtained prints, finishes, coats, coatings, moulded objects such as sheets, filaments, boards, blocks, granulates and rods colored in a brilliant red hue of excellent permanency.

The novel red pigment can also be used for coloring solid, elastic, pasty, viscous, low viscosity or thixotropic substances and can be incorporated therein by per se known methods. Aqueous pastes can conveniently be obtained by stirring the pigment in water, with or without the addition of a wetting agent or dispersant, or by stirring or kneading the pigment into a dispersant in the presence of water and, in some cases, of organic solvents or oils. These pastes can in turn be used for making flush pastes, printing inks, size colors, plastics dispersions and spinning solutions. The pigment can also be blended into water, organic solvents, non-drying oils, drying oils, paint systems and varnishes, plastics or rubber by stirring, rolling, kneading or grinding. Finally, it is also possible to process the pigment by dry mixing with organic or inorganic materials, granulates, fabrics, powders and other pigments to compositions.

The novel pigment is distinguished not only by purity of shade with very high saturation, good opacity and outstanding color strength, but also by good all round fastness properties such as fastness to light and weather, fastness to overspraying, fastness to migration and heat fastness, as well as good rheological properties.

The novel pigment is preferably suitable for coloring polyolefins and, in particular, water and/or solvent-borne paints, especially automotive lacquers.

The invention is illustrated by the following Examples.

EXAMPLE 1a)

9.2 g of sodium are added to 160 ml of dry tert-amyl alcohol and the mixture is heated to 100° C. and refluxed, with vigorous stirring, until the sodium is completely dissolved. The solution is cooled to 90° C., then 35.85 g of 4-biphenyl nitrile are added and the mixture is heated again to reflux temperature (c. 110° C.). Then 24.4 g of diisopropyl succinate are slowly added (ca. 6 ½ hours) and the suspension is refluxed for another 2 hours, cooled to 100° C., and diluted with 20 ml of tert-amyl alcohol.

b) The pigment salt suspension so obtained is added to a mixture of 70 ml of water and 490 ml of n-propanol. The mixture is then stirred for 6 hours at 85° C., cooled to 40° C. and filtered. The residue is washed first with methanol until the filtrate is colourless and then with water, likewise until the filtrate is colourless, and dried in a vacuum drying oven at 80° C., giving 27.5 g of a red product of formula

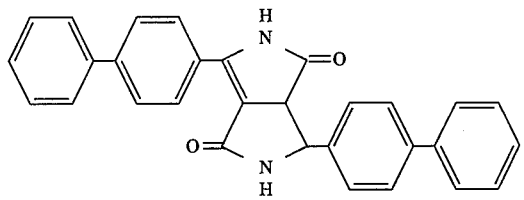

in powder form.

In accordance with the method described in DIN 53 775, part 2, a plasticised PVC pressed sheet with a thickness of 1.0 mm is prepared (cf. item 6.3 of DIN 53 775, part 2) having a pigment concentration of 1%, and the colour values are determined according to CIELAB.

The values obtained are as follows:

$L^*=38.4$, $C^*_{ab}= 48.1$, $h_{ab}= 25.0$

EXAMPLE 2a)

26.7 g of sodium are added to 460 ml of dry tert-amyl alcohol and the mixture is heated to 100° C. and refluxed, with vigorous stirring, until the sodium is completely dissolved. The solution is cooled to 90° C., then 105.3 g of 4-biphenyl nitrile are added and the mixture is again heated to reflux temperature (ca. 110° C.). Then 70.4 g of diisopropyl succinate are slowly added, while a mixture of tert-amyl alcohol and isopropanol (334 g) is removed continuously by distillation and simultaneously replaced with 335 g of tert-amyl alcohol.

b) The pigment salt suspension so obtained is cooled and added to a mixture of 1450 ml of ethanol and 290 ml of water. The mixture is then stirred for 6 hours under reflux, then cooled to 40° C. and filtered. The residue is washed first with methanol until the filtrate is colourless and then with water, likewise until the filtrate is colourless, and dried in a vacuum drying oven at 80° C., giving 107 g of the same red product as in Example 1.

In accordance with the method described in DIN 53 775, part 2, a plasticised PVC pressed sheet with a thickness of 1.0 mm is prepared (cf. item 6.3 of DIN 53 775, part 2) having a pigment concentration of 1%, and the colour values are determined according to CIELAB.

The values obtained are as follows:

$L^*=39.2$, $C^*_{ab}= 50.3$, $h_{ab}= 25.1$

EXAMPLE 3

The pigment salt suspension is prepared as described in Example 1a) and added to a mixture of 500 ml of isopropanol and 100 ml of water. The resultant suspension is heated in an autoclave for 5 hours at 120° C., then cooled to room temperature, filtered, and the filtrate is washed as described in Example 1 and dried. Yield: 30.0 g of the red pigment in powder form.

In accordance with the method described in DIN 53 775, part 2, a plasticised PVC pressed sheet with a thickness of 1.0 mm is prepared (cf. item 6.3 of DIN 53 775, part 2) having a pigment concentration of 1%, and the colour values are determined according to CIELAB.

The values obtained are as follows:

$L^*=36.9$ $C^*_{ab}=46.4$, $h_{ab}23.5$

EXAMPLES 4 and 5

A mixture of 230 g of glass beads (Ø= 2 mm)

92 g of a thermosetting acrylic varnish consisting of 57.80 g of acrylic resin ®URACRON 2263 XB, 50% in xylene/butanol (Chem. Fabrik Schweizerhalle), 10.35 g of melamine resin ®CYMEL 327 90% in isobutanol (Dyno Cyanamid), 5.50 g of butyl glycol acetate 11.40 g of xylene 3.30 g of n-butanol 1.00 g of silicone oil, 1% in xylene 2.65 g of dispersant ®Disperbyk 160 (Byk Chemie) and 8 g of pigment are dispersed for 90 minutes in a dispersing machine. The glass beads are separated and the pigmented lacquer is sprayed on aluminium sheets. The lacquer is dried in the air for 30 minutes at room temperature and then stoved for 30 minutes at 115° C.

The $C^*_{ab}$, $L^*$ and $h_{ab}$ values of the finishes obtained are determined according to the CIELAB system and are shown in the following Table.

| Example | Pigment | $C_{ab}^*$ | $L^*$ | $h_{ab}$ |
| --- | --- | --- | --- | --- |
| 4 | of Example 1 | 45.3 | 37.0 | 23.4 |
| 5 | of Example 2 | 47.5 | 38.6 | 24.7 |

All the coloristic measurements were done with a Minolta

What is claimed is:

1. A pigment form of the diketopyrrolopyrrole of formula

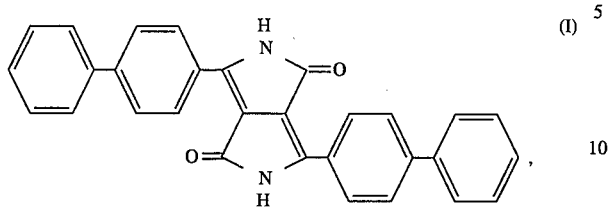
(I)

having high saturation, characterised by a chroma $C^*_{ab}$ of at least 45 in the CIELAB system in a full-shade plasticised PVC pressed sheet prepared in accordance with DIN 53 775, part 2, and having a pigment concentration of 1% and a thickness of 1.0 mm.

2. A pigment form according to claim 1, characterised by
 a chroma $C^*_{ab}$ of at least 46,
 a lightness $L^*$ of at least 36, and
 a hue angle $h_{ab}$ of at least 23.

3. A pigment form according to claim 1, characterised by
 a chroma $C^*_{ab}$ from 46.3 to 54,
 a lightness $L^*$ from 36.5 to 42, and
 a hue angle $h_{ab}$ from 23.4 to 29.

4. A process for the preparation of the highly opaque pigment form of the diketopyrrolopyrrole of formula

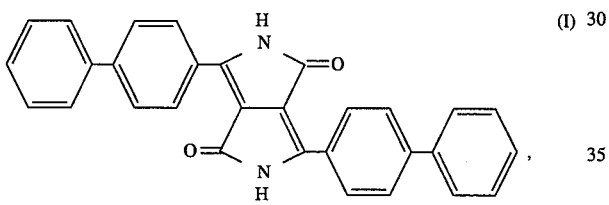
(I)

having high saturation, characterized by a chroma $C^*_{ab}$ of at least 45 in the CIELAB system in a full-shade plasticised PVC pressed sheet prepared in accordance with SIN 53775, part 2, and having a pigment concentration of 1% and a thickness of 1.00 mm, comprising reacting in a molar ratio of 1 to 2, a dicyclohexyl succinate, dialkyl succinate, monoalkyl-monophenyl succinate or diphenyl succinate, in which the succinate's alkyl group(s) is/are selected from $C_1$–$C_{18}$alkyl and phenyl is unsubstituted phenyl or phenyl which is substituted by one or two halogen atoms, one or two $C_1$–$C_6$alkyl or $C_1$–$C_6$alkoxy groups, with a nitrile of the formula

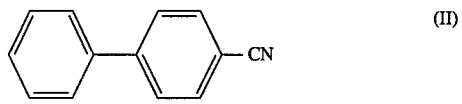
(II)

in an inert organic solvent and in the presence of an alkali metal or of an alkali metal alcoholate as strong base, at elevated temperature, to produce a pigment alkali metal salt, and subsequently generating a compound of formula I by protolysis of the resultant pigment alkali metal salt comprising adding, in a single portion, a suspension of said pigment alkali metal salt to water and an alcohol ROH, wherein R is $C_2$–$C_4$alkyl, in the temperature range from 65° to 150° C., and heating the pigment suspension for 30 minutes to 24 hours, and isolating a pigment of formula I.

5. A process according to claim 4, wherein the alcohol ROH is ethanol or n-propanol.

6. A process according to claim 4, wherein the pigment salt suspension is added to a mixture of water/alcohol in a ratio of water to alcohol of 5–50:95–50% by volume.

7. A process according to claim 4, wherein protolysis and conditioning are carried out in basic medium in the temperature range from 70° to 115° C. for 1 to 8 hours.

8. High molecular weight organic material containing a diketopyrrolopyrrole pigment of formula I according to claim 1.

9. High molecular weight organic material according to claim 8, which is a polyolefin.

10. High molecular weight organic material according to claim 8, which is a paint system.

11. High molecular weight organic material according to claim 1 0, which is an automotive lacquer.

* * * * *